United States Patent [19]

Boehringer et al.

[11] Patent Number: 5,133,703
[45] Date of Patent: Jul. 28, 1992

[54] PROCESS AND APPARATUS FOR COLLECTING BLOOD OF A PATIENT FOR AUTOTRANSFUSION

[75] Inventors: John R. Boehringer, Wynnewood; John Karpowicz, Glenmoore; Jeffrey Bence, Bensalem, all of Pa.

[73] Assignee: Boehringer Laboratories, Norristown, Pa.

[21] Appl. No.: 626,895

[22] Filed: Dec. 13, 1990

Related U.S. Application Data

[63] Continuation-in-part of Ser. No. 406,820, Sep. 13, 1989, which is a continuation of Ser. No. 264,444, Oct. 28, 1988, abandoned, which is a continuation of Ser. No. 906,750, Sep. 12, 1986, Pat. No. 4,781,707, which is a continuation-in-part of Ser. No. 830,533, Feb. 18, 1986, Pat. No. 4,767,417.

[51] Int. Cl.$^5$ .................. C02F 9/00; B01D 15/00; A61M 1/14; A61M 1/00
[52] U.S. Cl. .................. 604/317; 604/319; 604/4; 604/5; 604/6; 422/44; 210/256; 210/263; 210/502.1; 210/902; 210/692
[58] Field of Search .......... 604/317, 319, 4-6; 422/44; 210/256, 263, 266, 282, 287, 501, 502.1, 501.36, 692, 693, 902, 908, 911

[56] References Cited

U.S. PATENT DOCUMENTS

| | | | |
|---|---|---|---|
| 4,505,703 | 4/1985 | Gaale et al. | 604/317 |
| 4,522,623 | 6/1985 | Laüterjühg | 604/319 |
| 4,775,482 | 10/1988 | Thurman | 604/4 |
| 4,954,251 | 9/1990 | Barnes et al. | 604/4 |
| 4,957,492 | 9/1990 | McVay | 604/319 |
| 4,988,799 | 1/1991 | Samson et al. | 162/16 |

*Primary Examiner*—Randall L. Green
*Assistant Examiner*—A. Paul Zuttarelli
*Attorney, Agent, or Firm*—Paul and Paul

[57] ABSTRACT

A process and apparatus is provided for collecting a patient's blood for re-use of autotransfusion, in which blood is collected from a patient and delivered for treatment in a container, outside the patient, for later re-use or retransfusion to the patient. The treatment given to the blood before autotransfusion may reside in treating the blood to resist coagulation, treating the blood for removal of fats from the blood, or in removing other substances from the blood. The treatment, insofar as it is used to cause the blood to resist coagulation, includes withdrawing calcium ions from the blood and replacing them with other ions in sufficiently small quantities that the amount of other substance that is added to the blood is not harmful, preferably by passing the blood through a bed of ion exchange polymeric resin material. Insofar as fats are moved from the blood, the treatment includes collecting blood from the patient and wicking fats from the blood by means of a hydrophobic lipophilic wick. Other treatments to the blood, which accomplish the removal of other substances from the blood will also be apparent.

24 Claims, 1 Drawing Sheet

U.S. Patent
July 28, 1992
5,133,703
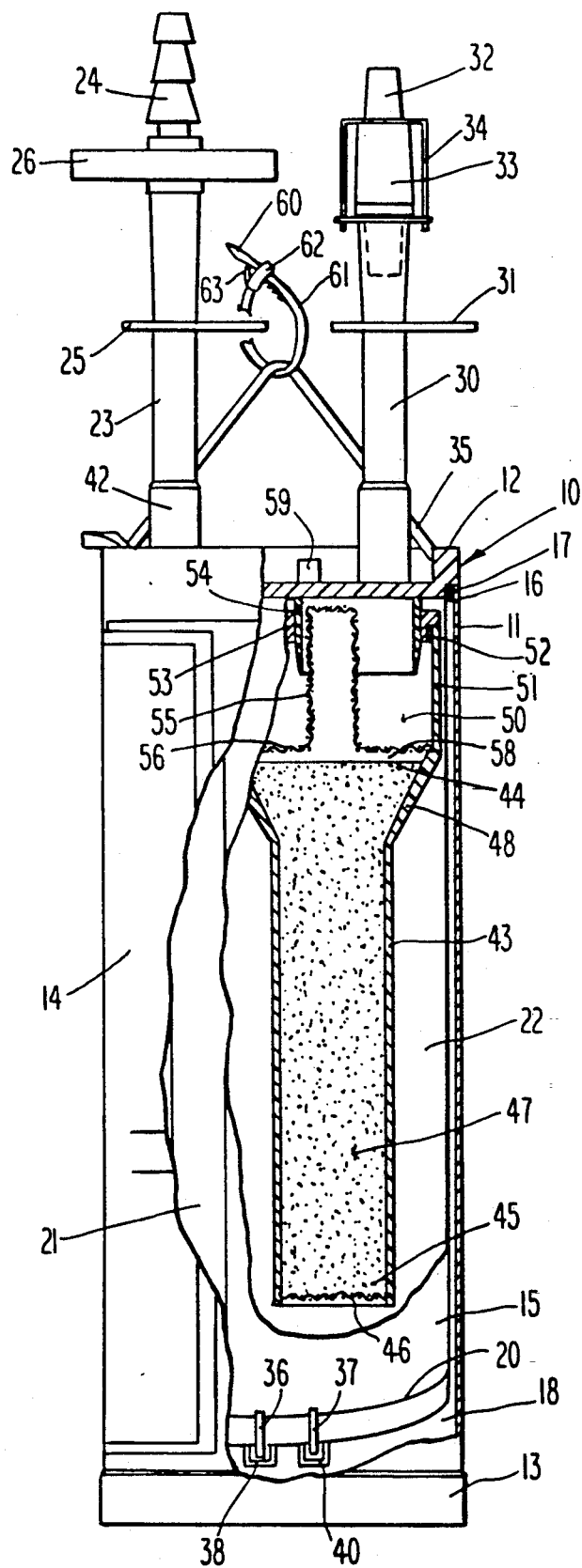
_Fig.1_
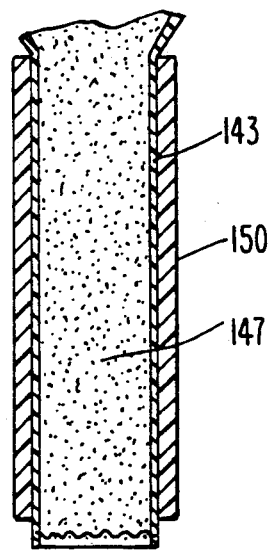
_Fig.2_

PROCESS AND APPARATUS FOR COLLECTING BLOOD OF A PATIENT FOR AUTOTRANSFUSION

CROSS-REFERENCE TO RELATED APPLICATIONS

This is a continuation-in-part of application Ser. No. 406,820 filed Sep. 13, 1989, and which is a continuation of application Ser. No. 264,444 filed Oct. 28, 1988, now abandoned, which is a continuation of application Ser. No. 906,750 filed Sep. 12, 1986; now U.S. Pat. No. 4,781,707, which is a continuation-in-part of application Ser. No. 830,533 filed Feb. 18, 1986; now U.S. Pat. No. 4,767,417.

BACKGROUND OF THE INVENTION

The present invention relates to a method and apparatus for treating blood for the removal of substances therefrom. This invention is directed to both post-operative and intra-operative blood treatment.

In both intra-operative and post-operative blood removal for autotransfusion, it has been found necessary to find some means to cause the blood to resist coagulation, because of the risk of clot formation resulting in harm to the patient upon autotransfusion. Largely, attempts at resisting coagulation have resulted in an anti-coagulant drug being injected into the container in which blood is being collected for re-use. Between intra-operative and post-operative blood re-use, post-operative blood collection for re-use has had increased medical interest, because the blood is generally freer of debris, contaminants and the like.

While there have been differing views on the extent to which anti-coagulants are necessary in post-operative blood collection for autotransfusion, the use of anti-coagulants has at least been a serious consideration, with due regard to individual predisposition to clotting, to the various operations/procedures being undergone by a patient which may affect on a relative basis the individual's ability to clot, and to the different procedures/operations as regards the likely rapidity of blood loss (loss rate).

It has been known, with regard to the above considerations, to adjust the anti-coagulant to these various factors.

It is also known that the injection of anti-coagulant into the blood, by means of injecting it into the container in which the blood is collected for re-use, or even the injection of anti-coagulants directly into the patient, can cause certain disadvantageous effects. One of these is citric toxicity. Another is an undesirable imbalance in pH (acidity/alkaline level of the blood). Yet another is dilution of the blood by the anti-coagulant, depending upon the blood condition at any given time. Yet another deficiency of using an anti-coagulant drug, is that the same must be periodically mixed. Another deficiency of using an anti-coagulant is the necessary careful control of the amount that is being added to the blood, which would vary depending upon the amount of blood being collected, among other variances.

SUMMARY OF THE INVENTION

The present invention, insofar as it is directed to reducing or preventing clot formation in blood for autotransfusion purposes, removes calcium from the blood by replacing it with sodium, potassium or magnesium (preferably sodium), by passing the blood through a bed of ion exchange polymeric resin material. In conjunction therewith, or separately therefrom, fats such as triglycerides, cholesterol, fatty acids and lipo-proteins may also be absorbed from the blood by wicking them out of the blood by contacting the blood with a wick that has a surface energy that will allow fatty substances to spread throughout the wick, but will not allow water or blood to spread or be absorbed into the wick. Such a wick will be a hydrophobic lipophilic material.

Accordingly, it is a primary object of this invention to provide a method and means for causing blood that is to be used for re-transfusion to a patient, to resist coagulation, without requiring the use of an anti-coagulant drug.

As a further object of this invention to accomplish the above object, wherein the resistance to coagulation is provided by replacing calcium ions in the blood with sodium, potassium or magnesium (preferably sodium) ions, by passing the blood through a bed of ion exchange polymeric resin material.

It is another object of this invention, to provide for the removal of fats from the blood.

It is a further object of this invention to accomplish the above object, by wicking fats from the blood by the use of a hydrophobic lipophilic wick for absorbing fats from the blood.

Other objects of the invention are provided by any of the above objects, wherein filters are provided for removing clots from the blood, wherein clots can be collected in a zone that spaces them from the blood that is being treated, whereby the treatments are effected during a partial vacuum-induced withdrawal of blood from the patient, and wherein the blood is connected in a container for ready re-use.

Other objects of the invention reside in the independent provision of any of the above-mentioned features.

It is yet a further object of this invention to provide identification for the blood-collection container, on an exterior surface thereof.

Other objects and advantages of the present invention will be readily apparent upon a reading of the following brief descriptions of the drawing figures, the detailed descriptions of the preferred embodiments, and the appended claims.

BRIEF DESCRIPTION OF THE DRAWINGS

FIG. 1 is a front elevational view of a blood collection apparatus in accordance with one embodiment of the present invention, wherein the apparatus includes an outside cylindrical vessel, an inside bag-like vessel and a blood coagulation resistance invention disposed inside the bag-like vessel, with portions of both the bag-like vessel and outer vessel being shown broken away, for clarity of illustration of the components inside the bag-like vessel, with the coagulation resistance components being shown in vertical section, for ease of illustration.

FIG. 2 is a fragmentary vertical sectional view of a portion of the blood coagulation-resisting components of FIG. 1, together with a fat-wicking sleeve disposed thereabout.

DETAILED DESCRIPTION OF THE PREFERRED EMBODIMENTS

Referring now to the drawings in detail, reference is first made to FIG. 1, wherein there is illustrated an apparatus generally designated by the numeral 10, for collecting blood of a patient for re-use. The apparatus 10 includes a generally cylindrical, somewhat rigid plastic canister 11, having closed upper and lower ends 12 and 13, respectively. On the exterior of the canister or vessel 11, is a label 14, provided with suitable instructions, and the ability for having indicia written thereon, such as patient identification, blood type, and other medical information, etc. Carried by the top closure 12, and inside the outer vessel 11, is an inner vessel 15 of the bag type, the upper end of which, 16, is hermetically sealed by bonding to the lid 12 of the canister 11. The upper end of the canister 11 is likewise hermetically sealed to the lid 12 via O-ring 17. Such hermetic seals allow, during assembly of the apparatus 10, for drawing a reduced pressure on the zone 18 between the vessels 11 and 15, to create a reduced pressure zone therebetween, prior to sealing closed the upper end of the vessel 11, to the container 12. Such hermetic seal allows the bag 15 to tend to hug the interior cyclindrical surface of the vessel 11. The bag 15 is provided with a lower end 20.

On the exterior of the bag 20 is an indicia surface 21 in the form of a generally vertically disposed adhesive label strip 21 or the like, to facilitate the nurse or other attendant writing the patient's name or other identifying indicia thereon, for proper identification at such time as the bag 15 is removed from the vessel 11, for re-use, as by re-transfusion to the patient.

Communicating with the interior zone 22 of the bag 15, is a vacuum draw conduit 23, connected to the zone 22 through the canister lid 12. The vacuum connection conduit 23 is provided with a connector 24, of generally conventional type, for connection to a source of lower pressure, such as to a partial vacuum pressure line normally available in hospital treatment rooms. One or more suitable shut-off clamps 25 are provided to clamp closed the flexible tubing 23, and thereby shut-off the drawing of vacuum from line 24 to the line 22, when it is not desired to draw a vacuum and draw blood from a patient into the zone 22.

A blood delivery line 30 is provided, also connected to communicate with the zone 22, through the lid 12. The line 30 is also of a flexible plastic tubing or the like, capable of being closed-off to prevent the passage of blood therethrough, by applying one or more shut-off clamps 31 thereto. Communicating with the blood flow line 30, is a line 32 for connection thereto at the upper end of the line 30, by means of a suitable fitting 33, with a band 34 holding the lower end of the tube 32 into the fitting to secure together the tubes or lines 32 and 30, for a sealing, non-leaking delivery line.

A hanger 35 is shown, carried by the upper closure 12, with the hanger being suitable to suspend the canister 11 from a conventional IV stand.

At the lower end 20 of the bag 15, there are provided conventional sealed spike ports 36 and 37, carried in their tabs 38 and 40, generally for invasion of the interior of the bag 15, for re-transfusion of the blood to the patient, after the bag 15 is removed from the canister 11, by insertion of a suitable needle or like conduit into one or more of the ports 36, 37, when autotransfusion is desirable.

At the upper end of the conduit 23, a hydrophobic filter 26 is provided, to facilitate drawing air through the line 23, when a vacuum is provided at 24, but for preventing the passage of blood through the fitting 42, in the event that the canister 11 should be upset or inverted for any reason. At the lower end of the conduit 23, a check valve (not shown) is provided to enable the device to maintain system vacuum when a temporary disconnect from a vacuum source is necessary.

The canister 11 and bag 15 and related portions of the apparatus 10 are constructed similar to corresponding components of U.S. Pat. No. 4,781,707, the complete disclosure of which is herein incorporated by reference herein.

Within the bag 15, there is provided a sleeve-like member 43 of generally vertically disposed cylindrical configuration, having an upper inlet 44 and a lower outlet 45. At the lower end, adjacent the outlet 45, is disposed a suitable mesh or like filter 46, of a selected opening size. The raising of blood through the sleeve will permit the desired interaction between the blood and an ion-exchange resin 47 disposed within the sleeve-like member 43. The filter 46, may, for example, be on the order of 170 microns in opening size, to in any event retain resin particles comprising the resin bed 47, above the filter 46.

The upper end of the sleeve-like member 43, is enlarged and, in the embodiment shown, is preferably of frusto-conical configuration as shown at 48, to conform in its largest, or opening size at the upper end thereof, to the size of an antechamber 50.

The sleeve-like member 43, and its frusto-conical entering portion 48, are generally of imperforate construction, to allow incoming blood to pass entirely therethrough, from the upper end of the sleeve-like member, out through the lower end at 45, thereof.

The ante-chamber 50 is constructed of an outer, generally cylindrical wall member 51 sealed at 52 to a ring 53 that is, in turn, hermetically sealed to an inlet sleeve opening 54 for the blood, such that blood delivered via line 30 must pass through the sleeve 54, into the ante-chamber 50 on its way into the frusto-conical inlet 48, and thereafter through the sleeve-like member 43.

Disposed within the ante-chamber 50, is an upstanding cylindrical filter 55, which functions as a pre-filter, to filter blood clots, bone particles and the like from blood that may rise up in the ante-chamber 50, above the level of the lower end 56 thereof. The lower end 56 of the ante-chamber, may, if desired, likewise comprise a non-porous material, or the same can be constructed to be of a porous filter material as shown.

When the lower end 56 of the ante-chamber 50 is of non-porous construction as shown, the only way in which blood can pass from the ante-chamber 50 to the interior 47 of the sleeve 43, is via the cylindrical filter 55. Thus, while blood may partially fill up the ante-chamber, and some portions of the filter 55 may become clogged with blood clots, bone pieces, and other debris that may be present in the blood, the use of an upstanding prefilter such as that 55, will allow a substantial vertical zone for accumulation of blood, clots and debris, yet permitting through-flow of blood into the zone 47 through the filter 55.

A space 58 is provided between the lower end 56 of the antechamber 50 and the upper end 44 of the entry to the sleeve-like member 43 that contains the resin, in order that any clots in the zone 54 will not come into contact with the resin material 47 in the sleeve 43, so that the resin material 47 is not wasted in removing clot-forming components from blood having clots therein, in the ante-chamber zone 50. Thus, the outlet of the filter 55, or any outlet of any kind from the ante-chamber 50 will not come into contact with the inlet end 44 of the sleeve containing the resin material 47 therein, but will remain spaced therefrom by an air gap provided by the spacing 58.

The ion exchange polymeric resin material 47 within the sleeve-like member 43 comprises a cation exchange resin preferably substantially completely of the sodium salt form thereof, although such could optionally be of the potassium or magnesium salt forms thereof, or of combinations of any of them, and upon blood coming into contact therewith, operates such that the calcium ion of the blood is substantially exchanged in the cation exchange resin in exchange for an equivalent amount of a monovalent cation such as sodium or potassium or another divalent cation such as magnesium.

The ion exchange resin may, if desired, be prepared in accordance with the teachings of U.S. Pat. No. 2,833,691, the disclosure of which is hereby incorporated herein by reference, except that for the present application, the cation exchange resin would preferably not comprise a potassium salt form thereof. The particles 47 within the sleeve 43 are thereby polymeric beads of the sodium, potassium or magnesium salt forms of a cationic ion exchange resin, to chemically remove calcium from the blood.

In order to facilitate emergency use, to hang the hanger 35 from any available device in the event that a suitable IV stand is not readily available, a flexible connector 60 is provided, having a bendable strip 61, adjustably connected through a catch mechanism 62, to hang the apparatus 10 from any available bed post, overhead support, or the like in emergency situations. The connector means will therefore be of the releasable type, having a release member 63, which when pulled open, or leftward as viewed in FIG. 1, will enable the end 60 to be withdrawn from connector member 62, to be re-applied after being disposed about a support structure.

With reference now to FIG. 2, it will be seen that another embodiment of the invention is presented, in which an apparatus 10 will be constructed preferably identical to that described above, but wherein the sleeve-like member 43 will be constructed as a sleeve-like member 143, having the same cation exchange resin 147 therein, as is 47 in FIG. 1, but wherein a generally cylindrical wick 150 is disposed about the outside surface of the sleeve member 143. Optionally, the sleeve-like member 43 or 143 itself could comprise the wick, constructed of a wick material as described below.

The wick 150 is adapted to remove fat, such as triglycerides, cholesterol, fatty acids and lipo-proteins from blood that enters the interior of a bag in which it is disposed, upon the blood building up from the lower end of the bag (not shown), around the exterior of the cylindrical wick 150. The wick is constructed of a hydrophobic lipophilic material, and it is comprised of a polymeric material selected from a group such as polyethylene, polypropylene, polystyrene, polyvinylchloride, tetrafluoroethylene and silicone, and most preferable it is comprised of the polymer polyethylene. The wick has a sufficient surface energy to allow a liquid, fatty substance to be absorbed and spread therein, but will not allow more hydrophilic constituents of the blood other than minor or trace amounts of such constituents of the blood to be absorbed and spread therein.

Irrespective of whether the apparatus of this invention employs one or both of the coagulation preventive resin 47 or the wick 150, or both, the upper end 12 of the canister may be provided with a sampling port 59 for periodically taking a sample of the blood for testing, or for the addition of reagents to blood, if desired.

It will be apparent from the foregoing that various modifications may be made in the details of construction, as well as in the use and operation of the device of the present invention, all within the spirit and scope of the invention as recited in the appended claims.

What is claimed is:

1. Apparatus for collecting blood of a patient for re-use, comprising:
   (a) a container for receiving blood from a body of a patient;
   (b) a delivery line for delivery patient blood to the container; and
   (c) means disposed in fluid communication with the container for causing the blood to resist coagulation, said means including a quantity of cation ion exchange polymeric resin material in sufficient amounts to replace calcium ions in the blood with monovalent or another divalent cation, with said quantity of ion exchange resin material being arranged in said container as a conduit for passage of blood therethrough, wherein said conduit includes a sleeve-like member having an inlet and an outlet, wherein said sleeve-like member has an elongate body and surrounds said quantity of ion exchange resin material, generally imperforate to blood passing therethrough, with perforate inlet and exit ends, wherein said inlet to said sleeve-like member has a portion of greater cross-sectional dimension than said elongate body.

2. The apparatus of claim 1, wherein said ion exchange polymeric resin material comprises a cation exchange resin substantially completely of the sodium salt form thereof, whereby the calcium ion of the blood is substantially substituted in the cation exchange resin in exchange for an equivalent amount of sodium ions.

3. The apparatus of claim 1, including suction means for drawing a negative pressure on said container for having patient blood drawn thereinto through said delivery line.

4. The apparatus of claim 1, including fat removal means disposed in the container, for removing fatty substances from the blood; said fat removal means including a hydrophobic lipophilic absorbing means for absorbing liquid fats from the blood.

5. The apparatus of claim 3, wherein said container comprises a generally flexible bag-like member, said flexible bag-like member having an interior and exterior.

6. The apparatus of claim 3, wherein said container comprises a first vessel disposed within a second vessel, to define a reduced pressure zone between the outside of the first vessel and the inside of the second vessel, with means hermetically sealing closed said zone.

7. The apparatus of claim 4, wherein said absorbing means is comprised of a polymeric material selected from the group consisting of polyethylene, polypropylene, polystyrene, polyvinylchloride, tetrafluoroethylene and silicone.

8. The apparatus of claim 4, wherein said absorbing means is comprised of a polymeric material.

9. The apparatus of claim 4, wherein said absorbing means is comprised of the polymer polyethylene.

10. The apparatus of claim 4, wherein said absorbing means comprises a material having a surface energy sufficient to allow a fatty substance to be absorbed and spread therein, but will resist more hydrophilic components of blood to be absorbed and spread therein.

11. The apparatus of claim 4, wherein said fat removal means is of generally sleeve-like construction, disposed about the elongate body which surrounds the quantity of ion exchange resin material.

12. The apparatus of claim 4, wherein said ion exchange polymeric resin material comprises a cation exchange resin substantially completely of the sodium salt form thereof, whereby the calcium ion of the blood is substantially absorbed on the cation exchange resin in exchange for an equivalent amount of sodium ions.

13. The apparatus of claim 4, including suction means for drawing a negative pressure on said container for having patient blood drawn thereinto through said delivery line.

14. The apparatus of claim 4, wherein said container comprises a generally flexible bag-like member, said flexible bag-like member having an interior and exterior.

15. The apparatus of claim 4, wherein an identification zone is provided on the exterior of said flexible bag-like member, including means for facilitating patient identification thereon.

16. The apparatus of claim 4, wherein said container comprises a first vessel disposed within a second vessel, to define a reduced pressure zone between the outside of the first vessel and the inside of the second vessel, with means hermetically sealing closed said zone.

17. The apparatus of claim 5, wherein an identification zone is provided on the exterior of said flexible bag-like member, including means for facilitating patient identification thereon.

18. The apparatus of claim 4, wherein said fat removal means comprises the conduit directly supporting said quantity of ion exchange material.

19. Apparatus for collecting blood of a patient for re-use, comprising:
 (a) a container for receiving blood from a body of a patient;
 (b) a delivery line for delivering patient blood to the container;
 (c) including fat removal means disposed in fluid communication with the container, for removing fatty substances from the blood; said fat removal means including a hydrophobic lipophilic absorbing means for absorbing liquid fats from the blood and
 (d) said fat removal means comprising an elongate wick member for contacting fatty substances in the blood and spreading the fatty substances therein.

20. The apparatus of claim 19, wherein said absorbing means is comprised of a polymeric material selected from the group consisting of polyethylene, polypropylene, polystyrene, polyvinylchloride, tetrafluoroethylene and silicone.

21. The apparatus of claim 19, wherein said absorbing means is comprised of the polymer polyethylene.

22. The apparatus of claim 19 wherein said absorbing means is comprised of a polymeric material.

23. The apparatus of claim 12, wherein said absorbing means comprises a material having a surface energy sufficient to allow a fatty substance to be absorbed and spread therein, but will not allow blood to be absorbed and spread therein.

24. The apparatus of any one of claims 1 and 19-23, including releasable connector means for attachment of the apparatus to a support.

* * * * *